(12) United States Patent
Hou et al.

(10) Patent No.: US 8,481,763 B2
(45) Date of Patent: Jul. 9, 2013

(54) PREPARATION PROCESS OF DRONEDARONE AND ITS SALTS

(75) Inventors: Xianshan Hou, Jiangsu (CN); Yongjiang Chen, Jiangsu (CN)

(73) Assignee: Jiangsu Hengrui Medicine Co., Ltd., Lianyungang, Jiangsu (CN)

( * ) Notice: Subject to any disclaimer, the term of this patent is extended or adjusted under 35 U.S.C. 154(b) by 0 days.

(21) Appl. No.: 13/701,642

(22) PCT Filed: Jun. 3, 2011

(86) PCT No.: PCT/CN2011/075255
§ 371 (c)(1),
(2), (4) Date: Dec. 3, 2012

(87) PCT Pub. No.: WO2011/153923
PCT Pub. Date: Dec. 15, 2011

(65) Prior Publication Data
US 2013/0072697 A1     Mar. 21, 2013

(30) Foreign Application Priority Data
Jun. 9, 2010 (CN) .......................... 2010 1 0195733

(51) Int. Cl.
*C07D 307/78* (2006.01)

(52) U.S. Cl.
USPC ...................................................... 549/468

(58) Field of Classification Search
USPC ...................................................... 549/468
See application file for complete search history.

(56) References Cited

U.S. PATENT DOCUMENTS

| 5,223,510 A | 6/1993 | Gubin et al. |
| 2005/0049302 A1 | 3/2005 | Gutman et al. |

FOREIGN PATENT DOCUMENTS

| WO | 03/048144 A2 | 6/2003 |

OTHER PUBLICATIONS

Int'l Search Report issued Sep. 8, 2011 in Int'l Application No. PCT/CN2011/075255.
He et al, "Graphical Synthetic Routes of Dronedarone Hydrochloride", Chinese Journal of Pharmaceuticals, vol. 41, No. 2, pp. 148-151 (Feb. 2010).

*Primary Examiner* — Kristin Bianchi
(74) *Attorney, Agent, or Firm* — Panitch Schwarze Belisario & Nadel LLP

(57) ABSTRACT

A process is provided for preparing dronedarone or pharmaceutically acceptable salts thereof. The process comprises reacting 5-amino-2-butyl-3-(4-[3-(dibutylamino)propoxy] benzoyl)benzofuran (compound A) with methanesulfonyl chloride without any catalyst to provide crude dronedarone hydrochloride, which is purified to afford highly pure product. Then, the dronedarone hydrochloride can be converted to highly pure dronedarone through treatment with an alkaline solvent, the dronedarone can be further converted to other pharmaceutically acceptable salts of dronedarone. In this process, acylation between compound A and methanesulfonyl chloride is carried out successfully and the formation of the dimethylsulfonyl by-product is inhibited.

19 Claims, No Drawings

PREPARATION PROCESS OF DRONEDARONE AND ITS SALTS

CROSS-REFERENCE TO RELATED APPLICATION

This application is a Section 371 of International Application No. PCT/CN2011/075255, filed Jun. 3, 2011, which was published in the Chinese language on Dec. 15, 2011, under International Publication No. WO 2011/153923 A1, and the disclosure of which is incorporated herein by reference.

FIELD OF THE INVENTION

The present invention relates to a novel process for preparing 2-butyl-3-(4-[3-(dibutylamino)propoxy]benzoyl)-5-methansulfonyl amino-benzofuran (dronedarone) and salts thereof, which are used in treatment of cardiovascular diseases.

BACKGROUND OF THE INVENTION

Dronedarone (SR33589) is a benzofuran derivative that is a new potent drug in the treatment of arrhythmia. Chemically, dronedarone is similar to amiodarone, but it has no iodine, so it is less lipophilic than amiodarone. Dronedarone not only retains the curative effects of amiodarone, but also has no extracardiac adverse response of amiodarone. It is expected to become a drug that is more safe, tolerated better by patients, and one alternative of amiodarone for the treatment of arrhythmia.

Along with the faster moving social modernization process and the higher social pressure people bear, the number of patients with cardiovascular disease in our country is increasing. Cardiovascular disease is listed as one of the top ten causes of death. Therefore, the development of dronedarone will bring great economic benefit and social benefit. Dronedarone is represented as formula [I]:

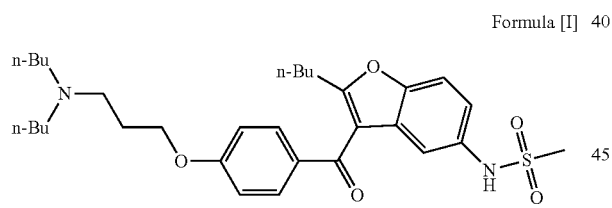

Formula [I]

U.S. Pat. No. 5,223,510A disclosed a process for preparing dronedarone as shown in scheme 1. In this patent, dronedarone is prepared by converting 2-butyl-5-nitrobenzofuran to 5-amino-2-butyl-3-(4-[3-(dibutylamino)propoxy]benzoyl)benzofuran (compound A) via acylation, hydrolysis, O-alkylation and reduction; then reacting the compound A with methanesulfonyl chloride in the presence of triethylamine as a catalyst to obtain acyl compound; and then purifying the acyl compound by column chromatography. Finally, dronedarone hydrochloride is obtained by treating dronedarone with hydrogen chloride-ether in ethyl acetate.

Scheme 1:

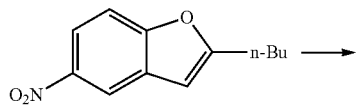

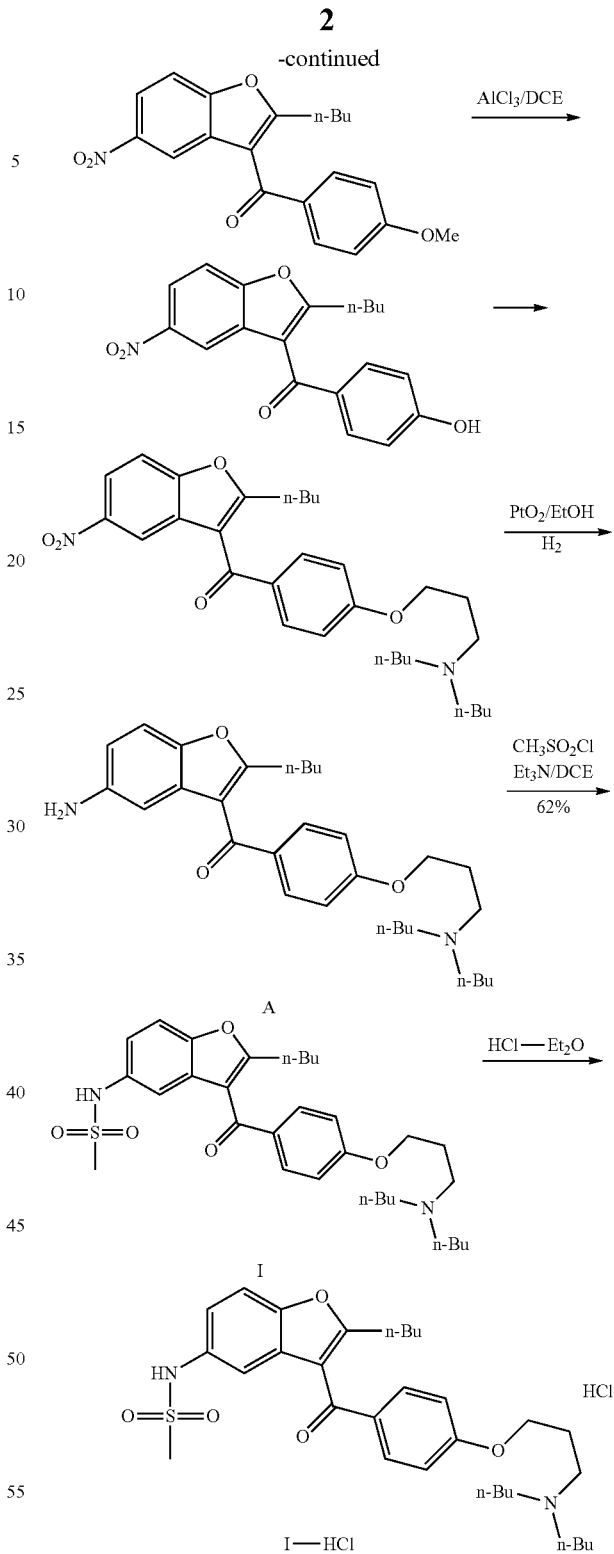

In this process, the compound A is reacted with methanesulfonyl chloride to easily obtain the undesired double methanesulfonyl compound (a compound of formula Ia), which requires a further purification of dronedarone by column chromatography. It is not very economic for industrial production. In addition, an additional salifying step of dronedarone hydrochloride is needed which costs more reaction equipment and reduces overall yield, and increases production costs at the same time.

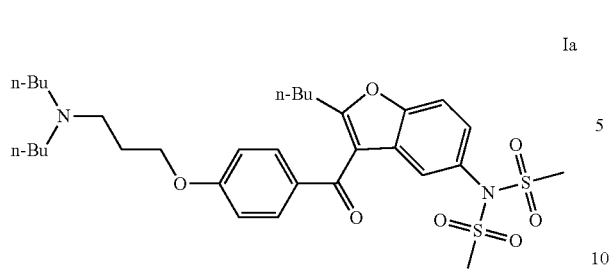

Ia

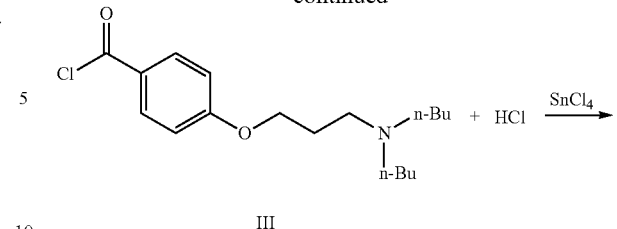

III

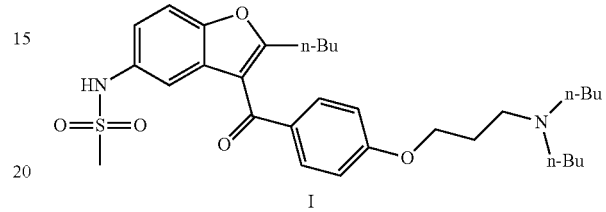

I

Many processes for the acylation of amines have been reported. U.S. Pat. No. 5,223,510A also disclosed that double methanesulfonyl compound IIa, not monomethyl sulfonyl compound (II), is obtained by reacting 5-amino-2-butyl-benzofuran in carbon tetrachloride with methanesulfonyl chloride in the presence of triethylamine as a catalyst. Compound IIa can be converted to compound II via deacylation with an additional deacylation step, which also increases the production cost, and is unfavorable for industrialized production. It is shown in scheme 2:

Scheme 2:

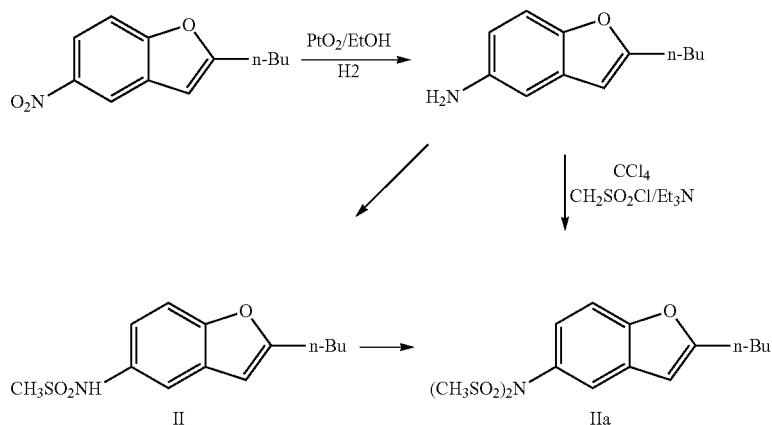

WO 03/048144A2 reported a process for preparing compound II by adjusting the proportion of compound II and compound IIa under different catalysts to an optimized condition (5<Pka<10) by using 2-butylbenzofuran-5-amine.

Subsequently, US2005049302 described a process for preparing compound II, not compound IIa, from 5-amino-2-butyl-benzofuran. In this process, compound II is reacted with compound III in the presence of tin tetrachloride (scheme 3) to obtain dronedarone with low yield and complicated operations, such as column chromatography etc., which is not suitable for industrial production.

Scheme 3:

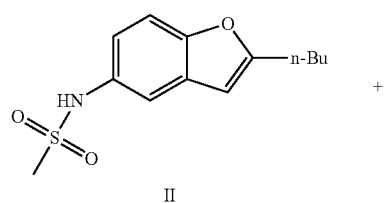

Therefore, it is more beneficial to get a process for preparing dronedarone and salts thereof having simple operation, high yield, low cost, and suitable for industrialized production.

DESCRIPTION OF THE INVENTION

In order to overcome the disadvantages of the prior art, the purpose of the present invention is to provide a novel process for preparing dronedarone and salts thereof with less steps, high yield, simple operation, and suitable for industrial production.

The invention relates to a process for preparing dronedarone hydrochloride, which comprises reacting 5-amino-2-butyl-3-(4-[3-(dibutylamino)propoxy]benzoyl)benzofuran (compound A) with methanesulfonyl chloride to provide dronedarone hydrochloride directly, wherein no catalyst is added to the reaction. Preferably, the process is carried out in the presence of one solvent or a mixture of multiple solvents. More preferably, the process further comprises purifying the crude dronedarone hydrochloride to obtain highly pure product thereof.

The invention also relates to a novel process for preparing dronedarone and a salt thereof, wherein the salt is not the hydrochlorate salt. The process comprises reacting 5-amino-2-butyl-3-(4-[3-(dibutylamino)propoxy]benzoyl)benzofuran (compound A) with methanesulfonyl chloride to provide dronedarone hydrochloride; and then converting the dronedarone hydrochloride to highly pure dronedarone via treatment with an alkaline solution, or based on the need, converting to other pharmaceutically acceptable salts of dronedarone. It is shown in scheme 4:

Scheme 4:

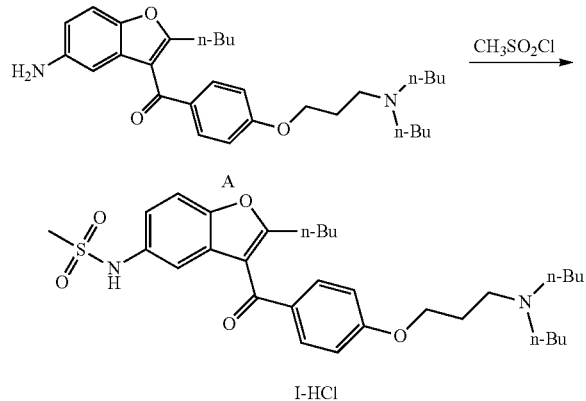

I-HCl

More specifically, this process for preparing dronedarone and its salts comprises the following steps:
a) acylating 5-amino-2-butyl-3-(4-[3-(dibutylamino)propoxy]benzoyl)benzofuran (compound A) with methanesulfonyl chloride without any catalysts to provide crude dronedarone hydrochloride, preferably in the presence of one or mixtures of more solvents;
b) purifying the crude dronedarone hydrochloride to obtain highly pure dronedarone hydrochloride, or further converting to highly pure dronedarone via alkaline solution, or subsequently converting to other pharmaceutically acceptable salts of dronedarone.

Surprisingly, the present inventors have found that an acylation between compound A and methanesulfonyl chloride can be carried out directly without any catalysts to provide highly pure dronedarone hydrochloride, and the formation of the dimethylsulfonyl byproduct (compound Ia) is significantly inhibited. Thus, a new synthetic method for the preparation of dronedarone and its salts is obtained.

The present inventors have found that the acylation between compound A and methanesulfonyl chloride can be carried out successfully in the presence of a solvent such as nitriles, ketones, halogenated hydrocarbons, ethers or aromatic hydrocarbons, or mixtures of any two or more solvents stated above without any catalysts. Furthermore, highly pure dronedarone can be directly obtained without any complicated operations such as column chromatography and the additional salifying process. If desired, dronedarone hydrochloride can be subsequently converted to other pharmaceutically acceptable salts of dronedarone.

As used herein, the term "catalyst" refers to any catalytic reagents used in the reaction of 5-amino-2-butyl-3-(4-[3-(dibutylamino)propoxy]benzoyl)benzofuran (compound A) with methane-sulfonyl chloride, such as an acid acceptor, including organic alkalis such as alkylamines like triethylamine, dipropylamine etc.; and inorganic alkalis such as alkali metals and alkaline earth metal salts like sodium carbonate, potassium carbonate, sodium bicarbonate, sodium hydroxide, calcium hydroxide, barium hydroxide etc.

Nitrile used in the invention is selected from the group consisting of $C_2$~$C_6$ aliphatic nitriles such as acetonitrile, propionitrile, butyronitrile and the like, preferably acetonitrile.

Under a temperature range from room temperature to reflux temperature, preferably reflux temperature, 5-amino-2-butyl-3-(4-[3-(dibutylamino)propoxy]benzoyl)benzofuran is reacted with methanesulfonyl chloride in acetonitrile solvent to provide a crude dronedarone hydrochloride, wherein an amount of acetonitrile used is in the range of 0 to 10 parts by volume, preferably 1 to 8 parts by volume, more preferably 3 to 6 parts by volume based on 1 part by weight of the compound A, and an amount of methanesulfonyl chloride used is in the range of 1 to 5 equivalents, and preferably 1.1 to 3 equivalents, and more preferably 1.2 to 2.5 equivalents relative to the compound A to obtain a reaction mixture. When the reaction is terminated, the reaction mixture is cooled to −30 to 50° C., preferably −20 to 35° C., more preferably −15 to 25° C. to obtain crude dronedarone hydrochloride. Then the crude dronedarone hydrochloride can be purified to obtain highly pure dronedarone hydrochloride. If desired, the obtained dronedarone hydrochloride can be converted to highly pure dronedarone via alkaline solvent, or further converted to other pharmaceutically acceptable salts of dronedarone.

Ketone used in the invention is selected from the group consisting of $C_3$~$C_6$ aliphatic ketones, preferably acetone.

Under a temperature range from room temperature to reflux temperature, preferably reflux temperature, 5-amino-2-butyl-3-(4-[3-(dibutylamino)propoxy]benzoyl)benzofuran is reacted with methanesulfonyl chloride in acetone solvent to provide a crude dronedarone hydrochloride, wherein an amount of acetone used is in the range of 0 to 15 parts by volume, preferably 4 to 10 parts by volume, more preferably 5 to 8 parts by volume based on 1 part by weight of the compound A, and an amount of methanesulfonyl chloride used is in the range of 1 to 5 equivalents, and preferably 1.5 to 3.5 equivalents, and more preferably 2 to 2.5 equivalents relative to the compound A to obtain a reaction mixture. When the reaction is terminated, the reaction mixture is cooled to −30 to 55° C., preferably −15 to 40° C., more preferably −10 to 25° C. to obtain crude dronedarone hydrochloride. Then the crude dronedarone hydrochloride can be purified to obtain highly pure dronedarone hydrochloride. If desired, the obtained dronedarone hydrochloride can be converted to highly pure dronedarone via alkaline solvent, or further converted to other pharmaceutically acceptable salts of dronedarone.

Halogenated hydrocarbon used in the invention is selected from the group consisting of $C_1$~$C_6$ aliphatic halogenated hydrocarbons, such as dichloromethane, chloroform, tetrachloromethane and the like, preferably dichloromethane.

Under a temperature range from room temperature to reflux temperature, preferably reflux temperature, 5-amino-2-butyl-3-(4-[3-(dibutylamino)propoxy]benzoyl)benzofuran is reacted with methanesulfonyl chloride in dichloromethane solvent to provide a crude dronedarone hydrochloride, wherein an amount of dichloromethane used is in the range of 0 to 30 parts by volume, preferably 10 to 25 parts by volume, more preferably 15 to 20 parts by volume based on 1 part by weight of the compound A, and an amount of methanesulfonyl chloride used is in the range of 1 to 15 equivalents, and preferably 5 to 10 equivalents, and more preferably 6 to 9 equivalents relative to the compound A to obtain a reaction mixture. When the reaction is terminated, the reaction mixture is treated with alkaline reagent such as alkali metal hydroxides (such as sodium hydroxide), alkali metal carbonate or alkali metal bicarbonate such as sodium bicarbonate, preferably sodium bicarbonate. Then the obtained dronedarone is salified in the presence of hydrochloric acid in acetone solvent. Subsequently, the crude dronedarone hydrochloride is quickly crystallized. If desired, the crude dronedarone hydrochloride is purified to obtain highly pure dronedarone hydrochloride. Then the obtained dronedarone hydrochloride can be converted to highly pure dronedarone via alkaline solvent, or if desired, further converted to other pharmaceutically acceptable salts of dronedarone.

Ether used in the invention is selected from the group consisting of straight chain ethers, such as $C_1$~$C_6$ aliphatic ethers, preferably glyme, and cyclic ethers such as $C_2$~$C_4$ aliphatic cyclic ethers, preferably tetrahydrofuran.

Under a temperature range from room temperature to reflux temperature, preferably reflux temperature, 5-amino-2-butyl-3-(4-[3-(dibutylamino)propoxy]benzoyl)benzofuran is reacted with methanesulfonyl chloride in tetrahydrofuran solvent to provide a crude dronedarone hydrochloride, wherein an amount of tetrahydrofuran used is in the range of 0 to 15 parts by volume, preferably 3 to 12 parts by volume, more preferably 5 to 10 parts by volume based on 1 part by weight of the compound A, and an amount of methanesulfonyl chloride used is in the range of is 1 to 8 equivalents, and preferably 1.5 to 5 equivalents, and more preferably 2 to 3 equivalents relative to the compound A to obtain a reaction mixture. When the reaction is terminated, the reaction mixture is cooled to −25 to 50° C., preferably −15 to 40° C., more preferably −10 to 35° C. to obtain crude dronedarone hydrochloride. Then the crude dronedarone hydrochloride can be purified to obtain highly pure dronedarone hydrochloride. If desired, the obtained dronedarone hydrochloride can be converted to highly pure dronedarone via alkaline solvent, or further converted to other pharmaceutically acceptable salts of dronedarone.

Aromatic hydrocarbon used in the invention is selected from the group consisting of substituted or unsubstituted $C_6$~$C_{10}$ aromatics, such as toluene, ethylbenzene, and isopropylbenzene, preferably toluene.

The mixtures of the solvents in the present invention are mixtures of two or more solvents, which are selected from the group consisting of nitrile, ketone, halogenated hydrocarbons, ethers or aromatic hydrocarbons, preferably acetone and acetonitrile.

Under a temperature range from room temperature to reflux temperature, preferably reflux temperature, 5-amino-2-butyl-3-(4-[3-(dibutylamino)propoxy]benzoyl)benzofuran is reacted with methanesulfonyl chloride in a mixture of acetone and acetonitrile solvent to provide a crude dronedarone hydrochloride, wherein an ratio of acetone and acetonitrile used is in the range of 0~5:1 (v/v), preferably 0.2~3:1 (v/v), more preferably 0.5~1:1 (v/v), and an amount of methanesulfonyl chloride used is in the range of is 1 to 5 equivalents, and preferably 1.5 to 4 equivalents, and more preferably 2 to 3 equivalents relative to the compound A to obtain a reaction mixture. When the reaction is terminated, the reaction mixture is cooled to −40 to 50° C., preferably −15 to 40° C., more preferably −10 to 35° C. to obtain crude dronedarone hydrochloride. Then the crude dronedarone hydrochloride can be purified to obtain highly pure dronedarone hydrochloride. If desired, the obtained dronedarone hydrochloride can be converted to highly pure dronedarone via alkaline solvent, or further converted to other pharmaceutically acceptable salts of dronedarone.

The solvent of the invention used for the purification of dronedarone hydrochloride is a mixture of acetone and water having preferably a ratio of 30~5:1 (v/v).

As used herein, the "alkali" used in "alkaline solvent" when converting the crude dronedarone hydrochloride to highly pure dronedarone or its hydrochloride via purification or alkaline solvent, or if desired, further converted to other pharmaceutically acceptable salts of dronedarone is an inorganic alkali, such as sodium hydroxide, sodium carbonate or sodium bicarbonate, preferably sodium bicarbonate.

In short, in the present invention, in a single or mixed solvents, for example, nitriles, such as acetonitrile, ketones, such as acetone, halogenated hydrocarbons, such as methylene chloride, acylation between compound A and methanesulfonyl chloride is carried out successfully without any catalysts to provide crude dronedarone hydrochloride. Furthermore, the crude dronedarone hydrochloride is directly obtained without complicated operations, such as column chromatography and additional salifying process. According to the need, the crude dronedarone hydrochloride is purified to afford highly pure product. Then the dronedarone hydrochloride can be converted to highly pure dronedarone via alkaline solvent, or if desired, further converted to other pharmaceutically acceptable salts thereof.

The process of the present invention has less steps, high yield, simple operation, low cost, and is suitable for industrialized production etc, with remarkable social benefit and economic benefit.

PREFERRED EMBODIMENTS

This invention will be better understood with the following examples. Those skilled in the art will readily appreciate the present invention. The following examples are merely illustrative of the invention and should not be read as limiting the scope of the invention in any manner.

Unless otherwise noted, the abbreviations used in these examples are as follows:
HPLC: High Performance Liquid Chromatography
$^1$H-NMR: Hydrogen nuclear magnetic resonance spectroscopy
MS: Mass Spectrometry Preparation of the Starting Material Compound A 5-amino-2-butyl-3-(4-[3-(dibutylamino)propoxy]benzoyl)benzofuran (compound A) was prepared according to U.S. Pat. No. 5,223,510A.

Example 1

Step 1) Preparation of Crude Dronedarone Hydrochloride

In a 5 L flask, 480 g compound A (1 mol) and 1.7 L acetonitrile were added and heated to reflux to obtain a mixture. Then, 100 mL methanesulfonyl chloride (1.29 mol)/800 mL acetonitrile were added dropwise to the mixture within 25~30 min. The reaction was maintained at reflux for 8 h. Then, the reaction was naturally cooled to obtain a solid. The next day, the solid obtained was filtered and dried to obtain 530 g crude dronedarone hydrochloride. Yield: 89.2%, Purity of HPLC: 99.5%.

Step 2) Preparation of Dronedarone Hydrochloride

In a 5 L flask, 530 g crude dronedarone hydrochloride, 3 L acetone and 100 mL water were added and heated to reflux for dissolving completely. The reaction mass was cooled for crystallization in an ice water bath under automatic stirring. About 30 minutes later, lots of solid was precipitated. The solid obtained was filtered and washed with acetone and dried to obtain 440 g targeted compound. Yield: 83%, mp: 141.5~143° C., Purity of HPLC: 99.8%, MS: [M+H]$^+$ m/e 557.50.

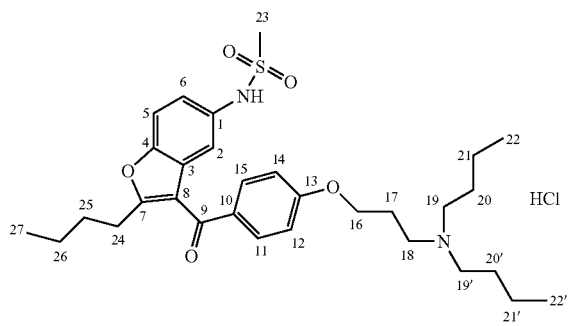 [SMILES: CCCCc1oc2ccc(NS(C)(=O)=O)cc2c1C(=O)c1ccc(OCCCN(CCCC)CCCC)cc1 ; Cl]

TABLE 1 dronedarone hydrochloride $^1$H-NMR data and assignments

| Chemical shift (ppm) | multi-plicity | The number of protons | Proton assignment | The chemical shifts of the relevant hydrogen (ppm) |
|---|---|---|---|---|
| 0.799-0.829 | t | 3 | 27 | 1.226-1.270 |
| 0.908-0.937 | t | 6 | 22, 22' | 1.323-1.368 |
| 1.226-1.270 | m | 2 | 26 | 0.799-0.829, 1.647-1.738 |
| 1.323-1.368 | m | 4 | 21, 21' | 0.908-0.937, 1.647-1.738 |
| 1.647-1.738 | m | 6 | 20, 20', 25 | 1.226-1.270, 1.323-1.368, 2.801-2.831, 3.036-3.079 |
| 2.230-2.262 | m | 2 | 17 | 3.209-3.250, 4.207-4.231 |
| 2.801-2.831 | t | 2 | 24 | 1.647-1.738 |
| 2.902 | s | 3 | 23 | |
| 3.036-3.079 | m | 4 | 19, 19' | 1.647-1.738, 11.0 |
| 3.209-3.250 | m | 2 | 18 | 2.230-2.262, 11.0 |
| 4.207-4.231 | t | 2 | 16 | 2.230-2.262 |
| 7.100-7.117 | d | 2 | 12, 14 | 7.793-7.811 |
| 7.240-7.262 | d | 1 | 6 | 7.613-7.631 |
| 7.307-7.311 | s | 1 | 2 | |
| 7.613-7.631 | d | 1 | 5 | 7.240-7.262 |
| 7.793-7.811 | d | 2 | 11, 15 | 7.100-7.117 |
| 9.660 | s | 1 | NH | Disappeared after exchange with D$_2$O |
| 11.0 | br | 1 | HCl | 3.036-3.079, 3.209-3.250, Disappeared after exchange with D$_2$O |

Example 2

Step 1) Preparation of Crude Dronedarone Hydrochloride

The procedure as described in step 1 of Example 1, with the difference that the reaction temperature was 55~60° C. and the reaction time was 15 h. Yield: 85.3%, Purity of HPLC: 99.0%.

Step 2) Preparation of Dronedarone Hydrochloride

The procedure as described in step 2 of Example 1. Yield: 81%, mp: 141~143° C., Purity of HPLC: 99.5%.

Example 3

Step 1) Preparation of Crude Dronedarone Hydrochloride

The procedure as described in step 1 of Example 1, with the difference that the reaction temperature was 40~45° C. and the reaction time was 41 h. Yield: 82.1%, Purity of HPLC: 98.3%.

Step 2) Preparation of Dronedarone Hydrochloride

The procedure as described in step 2 of Example 1, Yield: 80%, mp: 141~143° C., Purity of HPLC: 99.1%.

Example 4

Step 1) Preparation of Crude Dronedarone Hydrochloride

In a 5 L flask, 530 g compound A (1.1 mol) and 3 L acetone were added and heated to reflux. Then, 200 mL methanesulfonyl chloride (2.58 mol)/1 L acetone were added dropwise within 20 min. The reaction was maintained at reflux for 6 h. Then, the reaction was stirred overnight to obtain a white solid. The next day, the solid obtained was filtered and dried to obtain 473 g crude dronedarone hydrochloride. Yield: 72%, Purity of HPLC: 99.3%.

Step 2) Preparation of Dronedarone Hydrochloride

In a 5 L flask, 470 g crude dronedarone hydrochloride, 1550 mL acetone and 310 mL water were added and heated to reflux for dissolving completely. The reaction mixture was cooled for crystallization in an ice water bath under automatic stirring. About 1.5 h later, lots of solid was precipitated. The solid obtained was filtered and washed with acetone and dried to obtain 399.5 g of targeted compound. Yield: 84%, mp: 141.5~143.5° C., Purity of HPLC: 99.5%.

Example 5

Step 1) Preparation of Crude Dronedarone Hydrochloride

The procedure as described in step 1 of Example 4, with the difference that the reaction temperature was 40~45° C. and the reaction time was 48 h. Yield: 69%, Purity of HPLC: 98.8%.

Step 2) Preparation of Dronedarone Hydrochloride
The procedure as described in step 2 of Example 1. Yield: 83%, mp: 141~143° C., Purity of HPLC: 99.0%.

Example 6

Step 1) Preparation of Crude Dronedarone Hydrochloride 2.4 g compound A (5 mmol) were added to 30 mL methylene chloride and heated to reflux to obtain a mixture. Then, a solution of 3 mL methanesulfonyl chloride in 10 mL methylene chloride was added dropwise into the mixture within 20 min. The reaction was maintained at reflux for 26 h. Purity of HPLC of the mixture was measured as 95%. Then, the mixture was washed with saturated sodium bicarbonate solution to neutral, dried, filtered, and evaporated under reduced pressure to solid. 6 mL acetone and 1 mL hydrochloric acid were added to the solid under stirring for crystallization. The obtained solid was filtered and dried to obtain 2.1 g crude dronedarone hydrochloride. Yield: 70.8%, Purity of HPLC: 99%.

Step 2) Preparation of Dronedarone Hydrochloride

The procedure as described in step 2 of Example 1. Yield: 81%, mp: 141.5~143.5° C., Purity of HPLC: 99.5%.

Example 7

Step 1) Preparation of Crude Dronedarone Hydrochloride

In a 500 mL flask, 53 g compound A (0.11 mol) and 350 mL tetrahydrofuran were added and heated to reflux to obtain a mixture. Then, 20 mL methanesulfonyl chloride (0.26 mol)/40 mL tetrahydrofuran were added dropwise within 20 min. The reaction was maintained at reflux for 9 h. Then, the reaction was stirred overnight to obtain a solid. The next day, the solid obtained was filtered and dried to obtain 56.4 g crude dronedarone hydrochloride. Yield: 86%, Purity of HPLC: 98.8%.

Step 2) Preparation of Dronedarone Hydrochloride

In a 500 mL flask, 55 g crude dronedarone hydrochloride, 225 mL acetone and 22.5 mL water were added and heated to reflux for dissolving completely to obtain a mixture. The mixture was cooled in an ice water bath under automatic stirring. About 1 h later, lots of solid was precipitated. The solid obtained was filtered and washed with acetone and dried to obtain 45.1 g targeted compound. Yield: 82%, mp: 141.5~143.5° C., Purity of HPLC: 99.1%.

Example 8

Step 1) Preparation of Crude Dronedarone Hydrochloride

In a 5 L flask, 64 g compound A (0.13 mol), 1 L acetone and 1 L acetonitrile were added and heated to reflux to obtain a mixture. Then, 26 mL methanesulfonyl chloride (0.34 mol)/104 mL acetonitrile were added dropwise within 25~30 min. The reaction was maintained at reflux for 16 h. Then, the reaction mass was naturally cooled to obtain a solid. The next day, the solid obtained was filtered and dried to obtain 68 g crude dronedarone hydrochloride. Yield: 88.3%, Purity of HPLC: 99.1%.

Step 2) Preparation of Dronedarone Hydrochloride

The procedure as described in step 2 of Example 1. Yield: 82.5%, mp: 141.5~143° C., Purity of HPLC: 99.4%.

Example 9

Step 1) Preparation of Crude Dronedarone Hydrochloride

The procedure as described in step 1 of Example 7, with the difference that the reaction temperature was 40~45° C. and the reaction time was 36 h. Yield: 86.1%, Purity of HPLC: 98.8%.

Step 2) Preparation of Dronedarone Hydrochloride

The procedure as described in step 2 of Example 1. Yield: 82.5%, mp: 141.5~143° C., Purity of HPLC: 99.2%.

Example 10

Step 1) Preparation of Dronedarone 5.93 g dronedarone hydrochloride (0.01 mol) obtained in example 1 was dissolved in 40 mL methylene chloride to obtain a mixture. Then, the mixture was adjusted to neutral pH by adding saturated sodium bicarbonate solution. The organic layer was separated and washed with saturated sodium bicarbonate solution (10 mL×2), dried over sodium sulfate and evaporated under reduced pressure to get 5.61 g of oily product.

Step 2) Preparation of Dronedarone Sulfate

The obtained oily product was dissolved in 12 mL acetone to obtain a mixture, then 2 mL water were added to the mixture. Then, a solution of 1.1 mL concentrated sulfuric acid in 3 mL acetone was added dropwise under 10~15° C. in about 20 min. Then, the mixture was heated to 52° C. and stirred for 1 h. The mixture was cooled by ice water bath under stirring for crystallization. After about 3.5 h later, lots of solid was precipitated. The solid obtained was filtered and dried at 50° C. under vacuum to obtain 5.5 g targeted compound. Yield: 84%, (Calculation by dronedarone hydrochloride), Purity of HPLC: 99.85%.

Example 11

Step 1) Preparation of Dronedarone

The procedure as described in step 1 of Example 10.

Step 2) Preparation of Dronedarone Mesylate

The procedure as described in step 2 of Example 10, with the difference that the acid used was methanesulfonic acid (99%) (1.5 g) instead of concentrated sulfuric acid. Yield: 76%, Purity of HPLC: 99.83%.

Example 12

Step 1) Preparation of Crude Dronedarone Hydrochloride

In a 500 mL flask, 15 g compound A (0.03 mol) and 15 mL methanesulfonyl chloride (0.19 mol) were added and heated to 80° C. to obtain a mixture. The reaction was maintained at 80° C. for 5.5 h. The unreacted methanesulfonyl chloride was evaporated from the mixture under reduced pressure. 100 mL acetonitrile were added to dissolve the mixture, and the mixture was naturally cooled to obtain a solid. The next day, the solid obtained was filtered to obtain 13.5 g crude dronedarone hydrochloride. Yield: 72.5%, Purity of HPLC: 97.5%.

Step 2) Preparation of Dronedarone Hydrochloride

The procedure as described in step 2 of Example 1. Yield: 78.5%, mp: 140.5~142.5° C., Purity of HPLC: 98.9%.

What is claimed is:
1. A process for preparing dronedarone hydrochloride, wherein the process comprises reacting 5-amino-2-butyl-3-

(4-[3-(dibutylamino)propoxy]benzoyl)benzofuran with methanesulfonyl chloride to provide dronedarone hydrochloride, wherein no catalyst is added to the reaction.

2. The process according to claim 1, wherein the reaction between 5-amino-2-butyl-3-(4-[3-(dibutylamino)propoxy]benzoyl)benzofuran and methanesulfonyl chloride is carried out in one solvent or a mixture of multiple solvents.

3. The process according to claim 2, wherein the solvents are selected from the group consisting of a nitrile, ketone, halogenated hydrocarbon, ether and aromatic hydrocarbon.

4. The process according to claim 2, wherein the mixture comprises two or more solvents of the same or different kinds selected from the group consisting of a nitrile, ketone, halogenated hydrocarbon, ether and aromatic hydrocarbon.

5. The process according to claim 3, wherein the nitrile is selected from the group consisting of C2~C6 aliphatic nitriles.

6. The process according to claim 3, wherein the ketone is selected from the group consisting of C3~C6 aliphatic ketones preferably acetone.

7. The process according to claim 3, wherein the halogenated hydrocarbon is selected from the group consisting of C1~C6 aliphatic halogenated hydrocarbons, preferably dichloromethane.

8. The process according to claim 3, wherein the ether is selected from the group consisting of straight chain ethers and cyclic ethers.

9. The process according to claim 8, wherein the straight-chain ether is selected from the group consisting of C1~C6 aliphatic ethers, and the cyclic ether is selected from the group consisting of C2~C4 aliphatic cyclic ethers.

10. The process according to claim 3, wherein the aromatic hydrocarbon is selected from the group consisting of substituted and unsubstituted C6~C10 aromatic hydrocarbons.

11. The process according to claim 1, wherein the process further comprises a step of purification of the obtained dronedarone hydrochloride.

12. The process according to claim 11, wherein the solvent used for the purification of dronedarone hydrochloride is acetone/water.

13. A process for preparing dronedarone, comprising preparing dronedarone hydrochloride using the process according to claim 1; and converting the dronedarone hydrochloride to dronedarone via treatment with an alkaline solution.

14. A process for preparing a salt of dronedarone other than the hydrochlorate salt, comprising preparing dronedarone hydrochloride using the process according to claim 1; converting the dronedarone hydrochloride to dronedarone via treatment with an alkaline solution; and converting the dronedarone to the salt of dronedarone.

15. The process according to claim 14, wherein the alkali used in alkaline solution is an inorganic alkali.

16. The process according to claim 15, wherein the inorganic alkali is selected from the group consisting of sodium hydroxide, sodium carbonate and sodium bicarbonate.

17. The process according to claim 2, wherein the solvent is selected from the group consisting of acetonitrile, acetone, dichloromethane, 1,2-dimethoxyethane, tetrahydrofuran and toluene.

18. The process according to claim 12, wherein the acetone/water has a ratio of 30:1~5:1(v/v).

19. The process according to claim 16, wherein the inorganic alkali is sodium bicarbonate.

* * * * *